(12) United States Patent
Tian et al.

(10) Patent No.: US 8,094,149 B2
(45) Date of Patent: Jan. 10, 2012

(54) MULTI-SPECTRAL RECONSTRUCTION METHOD BASED ON ADAPTIVE FINITE ELEMENT

(75) Inventors: Jie Tian, Beijing (CN); Xin Yang, Beijing (CN); Yujie Lv, Beijing (CN); Chenghu Qin, Beijing (CN)

(73) Assignee: Institute of Automation of the Chinese Academy of Science, Beijing (CN)

( * ) Notice: Subject to any disclaimer, the term of this patent is extended or adjusted under 35 U.S.C. 154(b) by 975 days.

(21) Appl. No.: 12/075,233

(22) Filed: Mar. 10, 2008

(65) Prior Publication Data

US 2008/0259074 A1 Oct. 23, 2008

(30) Foreign Application Priority Data

Apr. 18, 2007 (CN) .......................... 2007 1 0098464

(51) Int. Cl.
*G06T 15/00* (2006.01)
(52) U.S. Cl. ........................................ 345/419; 382/131
(58) Field of Classification Search .................. None
See application file for complete search history.

(56) References Cited

U.S. PATENT DOCUMENTS

2007/0244395 A1* 10/2007 Wang et al. ................... 600/476

OTHER PUBLICATIONS

Contag et al., Advances In Vivo Bioluminescence Imaging of Gene Expression, *Annu. Rev. Biomed. Eng.* 2002 4:235-60.

Coquoz, et al., Determination of depth of in vivo bioluminescent signals using spectral imaging techniques, *Proceedings of SPIE*, vol. 4967 (2003) p. 37-45.
Dehghani, et al., Spectrally resolved bioluminescence optical tomography, *Optics Letter*, vol. 31, No. 3, (2006).
Diniz-Ehrhardt, et al., Comparing the numerical performance of two trust-region algorithms for large-scale bound-constrained minimization, *Investigacion Operativa*, vol. 7, No. 1-2, Jan.-Jun. 1997.
Gibson, et al., Recent advances in diffuse optical imaging, *Phys. Med. Biol.*, 50 (2005) R1-R43.
Martin Hanke, et al., Regularization methods for large-scale problems, *Surv. Math. Ind.* (1993) 3:253-315.
Joshi et al., Adaptive finite element based tomography for fluorescence optical imaging in tissue, *Optics Express*, vol. 12, No. 22 (2004), 5402-5417.

(Continued)

*Primary Examiner* — Ulka Chauhan
*Assistant Examiner* — Robert Bader
(74) *Attorney, Agent, or Firm* — Connor O'Connor (57) ABSTRACT

A multi-spectral reconstruction method based on adaptive finite element comprising the following steps: discretizing the diffusion equation in the object domain on the single spectral; establishing the relationship between the boundary measurement data and the unknown source variables on single spectral based on a posteriori permissible source region selection method, and forming the objective function based on the multi-spectral characteristics and the regularization method; optimizing the objective function and determining if the reconstruction shall be stopped or not; and if the reconstruction shall not be stopped, refining the mesh adaptively by using a posteriori measure method, and then returning to the first step to continue the reconstruction process. This method uses kinds of a priori information and the multi-spectral information, combined with the adaptive finite element method, proposes a posteriori permissible source region strategy, improves the reconstruction quality and speed of BLT availably, and reduces the ill-posedness of this imaging modality.

5 Claims, 3 Drawing Sheets

OTHER PUBLICATIONS

Alexandrakis, et al., Tomographic bioluminescence imaging by use of a combined optical-PET (OPET) system: a computer simulation feasibility study, Phys. Med. Biol. 50 (2005) 4225-4241.

Li, Hui, et al., A mouse optical simulation environment (MOSE) to investigate bioluminescent phenomena in the living mouse with the Monte Carlo method, *Academic Radiology*, vol. 11, No. 9 (2004), 1029-1038.

Lorensen, et al., Marching Cubes: A high resolution 3D surface construction algorithm, *Computer Graphics*, vol. 21, No. 4 (1987), 163-169.

Lv, Yujie, et al., A multilevel adaptive finite element algorithm for bioluminescence tomography, *Optical Society of America* (2006).

Massoud, Tank F., et al., Molecular imaging in living subjects: seeing fundamental biological processes in a new light, *Genes & Development* 17:545-580 (2003).

Ntziachristos, Vasilis et al., Diffuse optical tomography of highly heterogeneous media, *IEEE Transactions on Medical Imaging*, vol. 20, No. 6 (2001), 470-478.

Ntziachristos, Vasilis et al., Looking and listening to light: the evolution of whole-body photonic imaging, *Nature Biotechnology*, vol. 23 No. 3 (2005), 313-320.

Pogue, Brian W., et al., Comparison of imaging geometries for diffuse optical tomography of tissue, *Optics Express*, vol. 4, No. 8 (1999), 270-286.

Alexandrakis, et al., Effect of optical property estimation accuracy on tomographic bioluminescence imaging: simulation of a combined optical-PET (OPET) system, *Phys. Med. Biol.* 51 (2006) 2045-2053.

Ripoll, et al., Fast analytical approximation for arbitrary geometries in diffuse optical tomography, *Optics Letters*, vol. 27, No. 7 (2002), 527-529.

Ripoll, et al., Free-Space propagation of diffuse light: Theory and Experiments, *Phys. Rev. Letters*, vol. 91 No. 10, (2003).

Roy, et al., Active constrained truncated Newton method for simple-bound optical tomography, *J. Opt. Soc. Am.*, vol. 17, No. 9 (2000), 1627-1641.

Schweiger et al., The finite element method for the propagation of light in scattering media: Boundary and source conditions, Med. Phys. 22(11), Pt. 1, (1995), 1779-1792.

Wang, et al., Uniqueness theorems in bioluminescence tomography, *Med. Phys.* 31 (8), (2004), 2289-2299.

Ziji Wu, Accurate and efficient three-dimensional mesh generation for biomedical engineering applications, Worcester Polytechnic Institute, Dissertation (2001).

Wu, et al., Multiple material marching cubes algorithm, *Int. J. Numer. Meth. Engng* 2003; 58: 189-207.

Jürgen Bey, Tetrahedral Grid Refinement, *Computing*, vol. 55, No. 4, pp. 355-378 (1995).

Ye et al., Nonlinear multigrid algorithms for Bayesian optical diffusion tomography, *IEEE Transactions on Image Processing*, vol. 10, No. 5 (2001), 909-2001.

Zhao et al., Emission spectra of bioluminescent reporters and interaction with mammalian tissue determine the sensitivity of detection in vivo, *Journal of Biomedical Optics*, vol. 10(4) (2005).

Bhaumik et al., Optical imaging of *Renilla luciferase* reporter gene expression in living mice, *PNAS*, vol. 99, No. 1 (2002).

Birgin et al., Large-scale active-set box-constrained optimization method with spectral projected gradients, *Computational Optimization and Applications*, vol. 22, 101-125 (2002).

Bhaumik et al., Optical imaging of *Renilla* luciferase reporter gene expression in living mice, *PNAS*, vol. 99, No. 1 (2002).

Birgin, et al., Large-scale active-set box-constrained optimization method with spectral projected gradients, *Computational Optimization and Applications*, 22, 101-125 (2002).

Chaudhari et al., Hypersprctral and multispectral bioluminescence optical tomography for small animal imaging, *Phys. Med. Biol.*, 50, pp. 5421-5441 (2005).

Cong et al., Practical reconstruction method for bioluminescence tomography, *Optics Express*, vol. 13, No. 18 (2005).

Cong, et al., A practical method to determine the light source distribution in bioluminescent imaging, Department of Radiology, University of Iowa.

Cong et al., Geometrical modeling using multiregional marching tetrahedral for bioluminescence tomography, *Proc. of SPIE*, vol. 5744, (2005), 756-763.

Lv et al., Spectrally resolved bioluminescence tomography with adaptive finite element: methodology and simulation, *Phys. Med. Biol.*, 52 (2007), 1-16.

\* cited by examiner

MULTI-SPECTRAL RECONSTRUCTION METHOD BASED ON ADAPTIVE FINITE ELEMENT

BACKGROUND OF THE INVENTION

1. Field of the Invention

The invention involves to the technology of optical molecular imaging modality-Bioluminescence tomography (BLT), especially involving an adaptive-finite-element-based multi-spectral reconstruction.

2. Description of the Related Art

As a new optical molecular imaging modality, BLT has rapid development and extensive application. Because the current technique can only produce a two-dimensional image, researchers can not readily detect a variety of regions of interest, which would be detectable by the development of BLT. Bioluminescence tomography is ill-posed, which means that BLT solution generally is not unique. It is necessary to incorporate a priori information for accurate BLT reconstruction, and how to make reasonable use of a priori information need to be further considered.

With the development of BLT, kinds of a priori information have been used to reconstruct the source, such as the surface light intensity distribution, the internal anatomic structure of reconstruction region, the optical properties distribution, the spectral characteristics and the physical meaning of the bioluminescent light source. All of these severely affect the reconstructive results of the light source. Generally, existing reconstruction algorithm can be divided into two categories: one is based on a priori permissible source region; the other is based on multi-spectral. Through the combination of the surface light intensity distribution and the internal anatomic structure of reconstruction region, the region of source can be generally inferred, thus a better permissible source region less than the overall region can be obtained as initial region to solve the uniqueness problem of the reconstruction. The broad spectrum characteristics of bioluminescent light source are often used. Because materials in different optical spectra have different absorption and scatter coefficients, the detection of different spectra helps to accurately locate the source. It is worth mentioning that the relevant scientific literature expatiates that if only the multi-spectral information is considered and a heterogeneous reconstruction target is regarded as a homogeneous reconstruction target, the light source reconstruction, especially for a deep light source, is not sufficient.

The BLT considers the whole object as the reconstruction region, which will increase the computational burden, and also make it difficult to restrict the permissible results. In addition, with the introduction of multi-spectral and the development of the non-contact detection mode, the large-scale data set seriously affects source reconstruction speed. In the field of optical molecular imaging, although the analytical methods, which shall be able to significantly improve the computational speed, are well developed, it is not suitable to solve the region with complex inner structure. The numerical approaches are widely developed and used as flexible reconstruction methods, and some acceleration algorithms are also further studied, for example, the multi-mesh method. However, the multi-mesh method needs to uniformly refine the mesh of the whole region, which will not only result in great computational burden for BLT but is also unnecessary.

Finite element method is widely used in bioluminescence tomography. In view of the finite element analysis, the quality of BLT reconstruction is not only related to the signal-noise-ratio (SNR) of measured data but also to the discretization of the domain. To a large extent, the finer the discretized mesh becomes, the better the reconstruction is. However, the overly detailed mesh may aggravate the ill-posedness of the BLT problem and increase the numerical instability and computational cost. Compared with general finite element method, multi-spectral measurements, and anatomical and optical information first deal with the non-uniqueness of BLT and constrain the possible solution of source reconstruction in adaptive finite element multi-spectral reconstruction method. The use of adaptive mesh refinement and permissible source region based on a posteriori measures not only avoids the dimension disaster arising from the multi-spectral measured data but also reduces the ill-posedness of BLT and therefore improves the reconstruction quality.

SUMMARY OF THE INVENTION

For the sake of reducing the ill-posedness of BLT, the existing reconstruction methods using the multi-spectral measured data will not only bring in the dimensional disaster but also decrease the reconstruction speed and quality. To solve these issues, a novel multi-spectral reconstruction algorithm based on multilevel adaptive finite element is proposed in the invention.

The invention employs several kinds of a priori information to deal with the non-uniqueness of BLT. The introduction of the adaptive finite element method not only obtains local mesh refinement, but also develops a posteriori permissible source region strategy, both of which benefit the improvement of the reconstruction quality and the reduction of the ill-posedness. The steps of the approach are as follows.

To achieve the above objects, an adaptive-finite-element-based multi-spectral reconstruction method is provided in the present invention, comprising: performing the adaptive-finite-element-based multi-spectral reconstruction by utilizing a posteriori permissible source region selection strategy according to a priori knowledge about multi-spectral information of a bioluminescent source and an anatomical structure and optical parameters of a given domain to be reconstructed.

According to an embodiment of the present invention, the method comprises the following steps:

Step 1: on the $(l-1)^{th}$ ($l>1$) mesh level of the given domain to be reconstructed, a single-spectral diffusion equation is discretized into a linear equation system based on the finite element method;

Step 2: based on the selection of a posteriori permissible source region, linear relations between unknown source variables and boundary measured data are established on respective single-spectral bands, and the relations on the respective single-spectral bands are combined into a uniform equation reflecting the multi-spectral bands by using the spectral characteristic of the bioluminescent source;

Step 3: an optimization objective function is defined according to the regularization method, and then the spectral projected gradient-based large-scale optimization algorithm is used to optimize the objective function so as to obtain reconstructed results of the $(l-1)^{th}$ level;

Step 4: a single-spectral surface light density distribution is calculated with the aforementioned reconstructed results, and it is determined whether the reconstruction process shall be terminated or not according to stopping criteria, wherein if any one of the stopping criteria is satisfied, the reconstruction process is terminated;

Step 5: otherwise, if none of the criteria is satisfied, the permissible source region is reselected according to a posteriori error estimations, and the permissible and forbidden source regions are refined adaptively;

Step 6: the $(l-1)^{th}$ level is transformed into the $l^{th}$ level, the parameters are adjusted, and then the method returns to the Step 1 to continue the reconstruction process.

According to the embodiment of the present invention, the uniform equation reflecting the multi-spectral bands can be obtained by using the spectral characteristic of the bioluminescent source and a posteriori permissible source region selection strategy:

$$\Phi_l^{meas} = F_l W_l^S S_l$$

where $\Phi_l^{meas}$ and $S_l$ are respectively the boundary measured data and the unknown source variables of the $l^{th}$ level in the multi-spectral bands; $F_l$ expresses the relations between the boundary measured data and the unknown source variables in the multi-spectral bands; and $W_l^S$ is used to select a posteriori permissible source region, and further, these variables have the following concrete forms:

$$\Phi_l^{meas} = \begin{bmatrix} \Phi_l^{meas}(wb_1) \\ \Phi_l^{meas}(wb_2) \\ \vdots \\ \Phi_l^{meas}(wb_K) \end{bmatrix}, \quad F_l = \begin{bmatrix} \omega(wb_1)f_l(wb_1) \\ \omega(wb_2)f_l(wb_2) \\ \vdots \\ \omega(wb_K)f_l(wb_K) \end{bmatrix}$$

$$W_l^S = \text{Diag}\left(w_{l(11)}^S, w_{l(22)}^S, \ldots, w_{l(ii)}^S, \ldots, w_{l(N_{P_l} N_{P_l})}^S\right),$$

$$w_{l(ii)}^S = \begin{cases} 0 & \{s'_{l(i)} < \gamma_{sp}^{(l)} s_l'^{max}, l > 1\} \\ 1 & \{l = 1\} \text{ or } \{s'_{l(i)} \geq \gamma_{sp}^{(l)} s_l'^{max}, l > 1\} \end{cases}$$

where $\omega(wb_k)$ is the energy percentage of the $k^{th}$ discretized spectral band of the bioluminescent source, satisfying $$\omega(wb_k) \geq 0 \text{ and } \sum_{k=1}^{K} \omega(wb_k) \approx 1; \Phi_l^{meas}(wb_k)$$

and $f_l(wb_k)$ are the boundary measured data and the unknown source variables in the $k^{th}$ spectral band of the $l^{th}$ level respectively; and $s'_{l(i)}$ and $s_l'^{max}$ are the initial reconstructed results of the $l^{th}$ level which are obtained by interpolating the reconstructed results of the $(l-1)^{th}$ level and a maximum value respectively, that is:

$$S'_l = I_{l-1}^l S_{l-1}^r \quad (l>1)$$

where $\gamma_{sp}^{(l)}$ is the ratio factor to determine the size of the permissible source region of the $l^{th}$ level.

According to the embodiment of the present invention, it is determined whether the reconstruction process shall be terminated by considering the following three measure criteria: an error between the boundary measured data and the calculated value, a gradient $g_{\Phi_l}^{(l)}$ in the optimization of each level, and an upper limit of the reconstruction level l, in concrete:

$$\|\Phi_l^{meas}(wb_k) - \Phi_l^c(wb_k)\| \leq \epsilon_\Phi, \|g_{\Phi_l}^{(l)}\| \leq \epsilon_g \text{ or } l \geq L_{max},$$

where $\Phi_l^{meas}(wb_k)$ and $\Phi_l^c(wb_k)$ are the boundary measured data in the $k^{th}$ spectral band of the $l^{th}$ discretized level and the corresponding calculated value respectively; and $\epsilon_\Phi$, $\epsilon_g$ and $L_{max}$ are corresponding measurement thresholds respectively.

According to the embodiment of the present invention, in the permissible and forbidden source regions, a mesh to be refined is selected according to the hierarchical defect correction based a posteriori error estimation method and the direct maximum selection method respectively.

According to the embodiment of the present invention, in the forbidden source region, the selection of the mesh is performed by only using the error estimations in the single-spectral band, thereby accelerating the reconstruction process.

BLT still faces challenging problems. In this invention, a novel tomographic algorithm employing adaptive finite element and spectrally resolved measurement is proposed for BLT reconstruction. Based on the diffusion approximation model, this algorithm considers the heterogeneous characteristics of the small animal as well as the spectral information of the bioluminescent sources as a priori information which adequately deals with the non-uniqueness of BLT. The combination of a posteriori permissible region selection and adaptive mesh evolution not only improves the reconstruction quality and reduces the ill-posedness of BLT, but also avoids the dimensional disaster arising from the use of the spectrally resolved data. The spectral projected gradient-based large-scale optimization algorithm and related modifications improve reconstruction efficiency and robustness.

The present invention synthesizes two current dominant reconstruction methods for BLT, proposing a spectrally solved tomographic algorithm with a posteriori permissible source region selection. The use of adaptive mesh refinement and permissible source region based on a posterior measures not only avoids the dimension disaster arising from the multi-spectral measured data but also reduces the ill-posedness of BLT and improves the reconstruction quality. Therefore, this algorithm demonstrates great merits of application in the development of BLT.

DETAILED DESCRIPTION OF THE PRESENTLY PREFERRED EMBODIMENTS

In the following the reconstruction algorithm will be elaborated with reference to the drawings. The implementation described herein is for illustrative purposes only and is not intended to limit the range of the invention.

The reconstruction method of this invention includes the steps as follows:

(1) The triangle grid in the reconstruction region is segmented on the $(l-1)^{th}$ ($l>1$) level, and then the finite element method is used to discrete the diffusion equation into a linear equation on a single-spectrum, which will be convenient for the next process;

(2) In view of the linear relationship between unknown sources and known boundary measured data, the relations between them are established by the matrix transformation in the single spectral band. Afterwards, taking into account the spectrum characteristics of the bioluminescent sources and the selection of a posteriori permissible source region, all the relation equations in the single-spectrum are combined, and then an equation representing multi-spectral characteristics is formed;

(3) The regularization method is used to build the optimized object function and then spectral projected gradient-based large-scale optimization algorithm is employed to optimize the object function. The above problem can be solved and the $(l-1)^{th}$ level reconstructed results can be obtained;

(4) Whether the optimization is finished is judged by the maximum number of the iteration and the reduction of optimization gradient. When the optimization is finished, the boundary flux density on one single band is calculated using the above reconstructed results. Then, the stopping criteria are used to determine whether the reconstruction is finished. When one of the criteria is satisfied, the reconstruction will be terminated;

(5) If none of the criteria is satisfied, reselect the permissible source region and refine the mesh based on optimization results and a posteriori error estimations respectively. The permissible and forbidden source regions are also selected on the $l^{th}$ discretized level;

(6) Transform the necessary parameters from the $(l-1)^{th}$ level to the $l^{th}$ level, and then return to step (1) to continue reconstruction.

The key steps related to the method in this invention will be thoroughly explained as follows:

Step 1: the Diffusion Equation is Transformed to Linear Equation by Finite Element Method.

The mathematic model accurately representing photon transmission in the medium is the radiative transfer equation (RTE). Because RTE is an integro-differential equation, it is extremely computationally expensive. Fortunately, many medium are highly scattering so the diffusion equation is a good approximation to simulate the photon transmitting in the medium. When the bioluminescent imaging experiment is performed in a totally dark environment, the propagation of photons in the biological tissues can be modeled by a steady-state diffusion equation and Robin boundary condition. When the influence of light wavelength on tissues optical properties is considered, the following model is given:

$$-\nabla \cdot (D(x,\lambda)\nabla\Phi(x,\lambda)) + \mu_a(x,\lambda)\Phi(x,\lambda) = S(x,\lambda)(x \in \Omega)$$

where $\Omega$ is the domain of reconstruction, $\Phi(x,\lambda)$ denotes the photon flux density [Watts/mm$^2$], $S(x,\lambda)$ is the source energy density [Watts/mm$^3$], $\mu_a(x,\lambda)$ is the absorption coefficient [mm$^{-1}$], $D(x,\lambda)=1/(3(\mu_a(x,\lambda)+(1-g)\mu_s(x,\lambda)))$ is the optical diffusion coefficient, $\mu_s(x,\lambda)$ is the scattering coefficient [mm$^{-1}$], g is the anisotropy parameter, considering the mismatching between refractive index n in the domain of reconstruction and the refractive index n' in the outer medium, the boundary condition may be represented:

$$\Phi(x,\lambda) + 2A(x;n,n')D(x,\lambda)(v(x)\cdot\nabla\Phi(x,\lambda)) = 0 (x \in \partial\Omega),$$

in which v is the unit outer normal on the domain boundary $\partial\Omega$; $A(x;n,n') \approx (1+R(x))/(1-R(x))$, when the external medium is air, $R(x)$ can be approximated as $R(x) \approx -1.4399n^{-2} + 0.7099n^{-1} + 0.6681 + 0.0636n$; The measured quantity is the outgoing flux density $Q(x,\lambda)$ on $\partial\Omega$, i.e.:

$$Q(x,\lambda) = -D(x,\lambda)(v \cdot \nabla \Phi(x,\lambda)) = \frac{\Phi(x,\lambda)}{2A(x;n,n')}(x \in \partial\Omega)$$

In the practical experiment, if the outgoing flux is detected with the band-pass filter, the continuous spectral range of bioluminescent source is divided into several bands $wb_k \in [\lambda_k, \lambda_{k+1}]$, k=1, 2, . . . , K.

In adaptive finite element analysis, a sequence $\{T_1, \ldots T_l, \ldots\}$ of nested triangulations to the given domain $\Omega$ can be generated by local mesh refinement. $N_{T_l}$ elements and $N_{P_l}$ vertex nodes exist in each triangulation $T_l$, and the linear equation is formed by finite element method:

$$(K_l(wb_k) + C_l(wb_k) + B_l(wb_k))\Phi_l(wb_k) = F_l(wb_k)S_l(wb_k)$$

Step 2: Establish the Linear Relationship Between the Source Variables and the Surface Measurement Data In view of multi-spectral measurement, a direct relationship between boundary measurable photon density and unknown bioluminescent sources distribution is established using a posterior permissible source region strategy.

Now, only one single-band $wb_k$ is considered. $M_l(wb_k) = K_l(wb_k) + C_l(wb_k) + B_l(wb_k)$, where $M_l(wb_k)$ is a symmetric positive definite matrix. Considering the linear relationship between unknown sources variables $S_l(wb_k)$ and the boundary measured flux density $\Phi_l^{meas}(wb_k)$, thus:

$$\Phi_l^{meas}(wb_k) = f_l(wb_k)S_l(wb_k)$$

where $f_l(wb_k)$ can be established by removing those rows of $M_l(wb_k)^{-1}F_l(wb_k)$ corresponding to the non-measurable points. Furthermore, the energy percentage of each spectral band $wb_k$ can be determined by experimental spectral analysis of the bioluminescent sources, that is $S(wb_k) = \omega(wb_k)S$, where $$\omega(wb_k) \geq 0, \sum_{k=1}^{K} \omega(wb_k) \approx 1$$

and S donates the total source density. Taking into account the above spectral distribution and the selection of permissible source region, it can be obtained that:

$$\Phi_l^{meas} = F_l W_l^S S_l$$

where $$\Phi_l^{meas} = \begin{bmatrix} \Phi_l^{meas}(wb_1) \\ \Phi_l^{meas}(wb_2) \\ \vdots \\ \Phi_l^{meas}(wb_K) \end{bmatrix}, \quad F_l = \begin{bmatrix} \omega(wb_1)f_l(wb_1) \\ \omega(wb_2)f_l(wb_2) \\ \vdots \\ \omega(wb_K)f_l(wb_K) \end{bmatrix}$$

where $\Phi_l^{meas}$ is the boundary measured photon flux density and $S_l$ is the unknown source variables. $F_l$ can be established by removing those rows of $M_l(wb_k)^{-1}F_l(wb_k)$ corresponding to the non-measurable points. $W_l^S$ is a diagonal matrix for selecting the permissible source region, that is:

$$W_l^S = \text{Diag}\left(w_{l(11)}^S, w_{l(22)}^S, \ldots, w_{l(ii)}^S, \ldots, w_{l(N_{P_l}N_{P_l})}^S\right),$$

-continued $$w_{l(ii)}^S = \begin{cases} 0 & \{s'_{l(i)} < \gamma_{sp}^{(l)} s_l'^{max}, l > 1\} \\ 1 & \{l = 1\} \text{ or } \{s'_{l(i)} \geq \gamma_{sp}^{(l)} s_l'^{max}, l > 1\} \end{cases}$$

$s'_{l(i)}$ and $s_l'^{max}$ are the initial reconstructed results on the $l^{th}$ level which are obtained by interpolating the reconstructed results of the $(l-1)^{th}$ level and the corresponding maximum value, that is $$S'_l = I_{l-1}^l S_{l-1}^r \quad (l>1),$$

$\gamma_{sp}^{(l)}$ is the ratio factor which is used to define the size of permissible region on the $l^{th}$ level. By retaining those columns of $F_l W_l^S$ corresponding to the permissible source region, the following linear system is obtained:

$$A_l S_l^p = \Phi_l^{meas}.$$

Step 3: Define the Objective Function According to the Regularization Method and Select an Effective Optimization Method for Optimization so as to Obtain Reconstructed Results Although the linear relationship has been established between the unknown source and boundary measured photon flux density, which will lead to failure in solving the linear equation directly because $A_l$ is a severely ill-conditioned matrix. In view of the physical meaning of variable parameters, the objective function $\Theta_l(S_l^p)$ is defined with Tikhonov regulation method on the $l^{th}$ level:

$$\min_{0 \leq S_l^p \leq S_l^{sup}} \Theta_l(S_l^p) = \{\|A_l S_l^p - \Phi_l^{meas}\|_\Lambda + \lambda_l \eta_l(S_l^p)\}$$

where $S_l^{sup}$ is the $l^{th}$ level upper bound of the source density; $\Lambda$ is the weight matrix, $\|V\|_\Lambda = V^T \Lambda V$; $\lambda_l$ the regularization parameter; and $\eta_l(\cdot)$ the penalty function. The better reconstructed results can be obtained through selecting the appropriate optimization method. Therefore, the spectral projected gradient-based large-scale optimization algorithm is modified to solve the above problem. The following judgment criteria are used to test whether the optimization process should be stopped: the norm ratio of the current gradient $g_{\Theta_l}^i$ to the initial one $g_{\Theta_l}^0$ and the iterative number $N_i^{(l)}$ on each level. When $\gamma_{g_i}^{(l)} < \epsilon_g^{(l)}$ or $N_i^{(l)} > N_{max}^{(l)}$, optimization will stop and the reconstructed result can be obtained, where $\gamma_{g_i}^{(l)} = \|g_{\Theta_l}^i\|/\|g_{\Theta_l}^0\|$, $N_{max}^{(l)}$ is the maximum permissible iterative number permitted.

Step 4: Based on the Above Reconstructed Results, the Surface Source Distribution on the Detectable Points can be Calculated to Judge Whether the Reconstruction Should be Terminated. If the Reconstruction Does Not Stop, Some Meshes are Selected by Using a Posteriori Measurement and Then Refined:

When the optimization of level l stops, the source distribution $\Phi_l^c(wb_k)$ on the single-spectrum detectable points can be solved by using the optimized reconstructed result. Then, three measurement criteria are used to determine if the reconstruction stops, namely (1) the error between measurement data on the single spectrum and the computed value, (2) the gradient $g_{101}^{(l)}$ of every optimization and (3) the upper limit of reconstruction on the $l^{th}$ level. This calculation is described as follows:

$$\|\Phi_l^{meas}(wb_k) - \Phi_l^c(wb_k)\| < \epsilon_\Phi, \|g_{\Phi_l}^{(l)}\| < \epsilon_g \text{ or } l \geq L_{max},$$

where $\Phi_l^{meas}(wb_k)$ is the boundary measurement data on the single-spectrum; $\Phi_l^c(wb_k)$ is the computed value on the $l^{th}$ level; $\epsilon_\Phi$, $\epsilon_g$ and $L_{max}$ are the corresponding measurement thresholds, respectively. When the reconstruction does not stop, the reconstructed results are used to select the new permissible source region. In the permissible and forbidden area, two different methods are selected to select the element which is to be refined, which are the direct maximum selection method and hierarchical defect correction technique. Because the elements with higher values of the optimization results most likely represent actual source locations in the permissible source region, so these elements are selected for refinement to improve the reconstruction quality. Accounting the computational burden, multi-spectral property can be use as the a priori information, however, photon transport model and the computational error are identical in different spectral band when the bioluminescent photon propagates in the same biological tissue. Using the hierarchical defect correction technique in the forbidden source region to select the element to be refined can reduce the computation burden. That is:

$$\tilde{e}_{V_l}^{W_l}(wb_k) = D_{E_l}^{-1}(wb_k) r_{E_l}(wb_k)$$

where $\tilde{e}_{V_l}^{W_l}(wb_k)$ represents the approximate error indicator; $E_l$ is the space obtained by decomposition of the quadratic finite element space $W_l$ into $V_l$ and $E_l$; $D_{E_l}(wb_k)$ is the approximation to $M_{E_l}(wb_k)$, and $r_{E_l}(wb_k)$ denotes the iterative residual in the space $E_l$.

Step 5: Local Mesh Refinement for Discrete Regions.

Comparing to the overall mesh refinement method, the local mesh refinement method has its more complicated manner, which involves in the choice of basic element and the establishment of refinement rules in discrete regions. As triangle and tetrahedron are the basic shapes which are usually used to describe the complicated region, the tetrahedron is chosen as the basic element for the discretized regions. A reasonable triangulation to the given domain facilitates an implementation of the local mesh refinement. The key point of the local mesh refinement method is how to deal with the singular point which is yielded in refinement process and affecting the computation of finite element method. Here the so-called red-green refinement criterion is chosen. The selected tetrahedron is divided into eight son tetrahedral elements via red refinement, and then green closure is used to deal with the singular point which is yielded in red refinement by refining the neighbor element. So the local mesh refinement is accomplished.

Step 6: Transform the Parameters, Go to Step 1 for the Next Cycle of Reconstruction Through the above steps, the reconstruction on one level is accomplished. For the next level reconstruction, the parameters that are dependent with the level should be adjusted, then go to Step 1 to continue the reconstruction.

Figure 1:
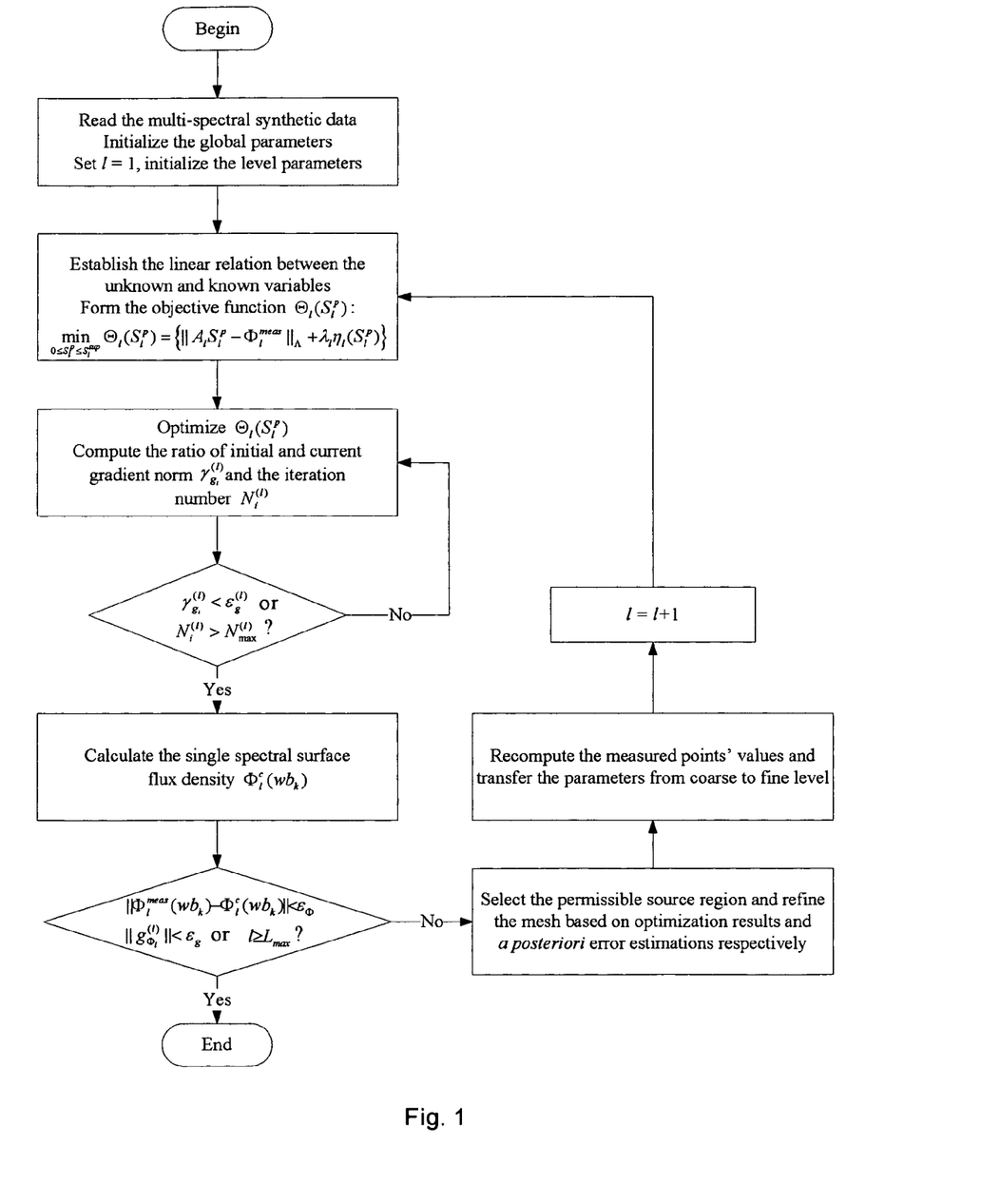
FIG. 1 is the flowchart of the proposed BLT tomographic algorithm.
Figure 2:
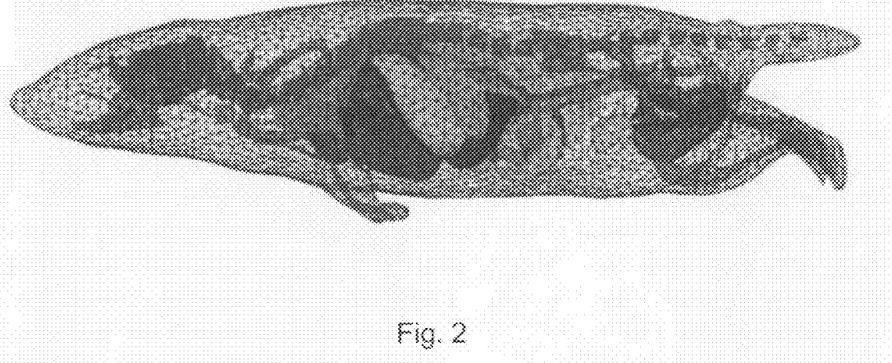
FIG. 2 is the view of the microMRI-based MOBY mouse phantom.

Results:

To validate the method, MicroMRI is used to establish a whole digital mouse (See FIG. 2) and boundary measurement data is produced by Monte Carlo Method for experiment.

In this experiment, the bioluminescent source, whose emitting-light is catalyzed by Luciferases in PC3M-Luc marked cells, is used as a reconstruction target. The radius of the source is 1 mm, and the power is 1 nW. For multi-spectral experiment, the spectrum region is from 500 nm to 750 nm, which is divided into 5 spectrum bands according to the current detecting level.

Apropos of the generation of the digital mouse model and the boundary measurement data, only the mouse torso, from the neck to the base of tail, is adopted as the model to generate the measurement data because of the lack of the brain optical parameters. The simulation software MOSE which is based on Monte Carlo method and developed by our lab is used to generate surface measurement data.

This multi-spectral platform uses the surface mesh of the mouse phantom with about 14600 triangle facets to generate the synthetic data. In the simulation, each spectral region of bioluminescent source is sampled by $1.0 \times 10^6$ photons. In the following experiments, a spherical source with 1.0 mm radius and 1.0 nano-Watts total power is used for verifications. In addition, the upper bound $S_{sup}^l$ is a sufficiently large positive number, the weight matrix $\Lambda$ is a unit matrix, and the penalty function is $\eta_l(X) = X^T X$. The gradient ratio tolerance $\epsilon_g^{(l)}$ and the maximum iteration number $N_{max}^{(l)}$ are invariable at each level, being equal to $1.0 \times 10^{-5}$ and 5000 respectively. The terminated gradient norm $\epsilon_g$, the stopping threshold $\epsilon_\Phi$, and the maximum number of mesh refinement $L_{max}$ are set to $7.0 \times 10^{-9}$, $1.0 \times 10^{-7}$ and 3 respectively. At the coarsest mesh level, the whole reconstruction object is the permissible source region. After mesh refinement, the selection factor $\gamma_{sp}^{(l)}$ is initially set to $10^{-4}$ for selecting the permissible source region. 1.5% and 50% of the reconstructed elements is refined in the permissible and the forbidden source regions respectively. The reconstruction procedure begins with an initial guess $S_{init}^{(l)}$ of $1.0 \times 10^{-6}$. All reconstructions are implemented on a PC with an Intel processor (Pentium 4 2.8 GHz) and a 1 GB of RAM.

Optical properties of biological tissues in mouse in different wavelength ranges used in the reconstruction are shown as the following table.

| | BAND | | | | | | | | | |
|---|---|---|---|---|---|---|---|---|---|---|
| | 500~550 nm | | 550~600 nm | | 600~650 nm | | 650~700 nm | | 700~750 nm | |
| | $\mu_a$* | $\mu'_s$* | $\mu_a$ | $\mu'_s$ | $\mu_a$ | $\mu'_s$ | $\mu_a$ | $\mu'_s$ | $\mu_a$ | $\mu'_s$ |
| BONE | 9.0e−3 | 3.34 | 2.2e−3 | 2.93 | 6.0e−4 | 2.61 | 3.6e−4 | 2.34 | 5.9e−4 | 2.11 |
| FAT | 6.2e−4 | 1.34 | 2.5e−4 | 1.28 | 2.1e−4 | 1.22 | 3.4e−4 | 1.18 | 1.2e−3 | 1.14 |
| HEART | 9.1e−3 | 1.28 | 2.2e−3 | 1.13 | 6.9e−4 | 1.00 | 5.8e−4 | 0.91 | 1.4e−3 | 0.82 |
| INTESTINE | 1.7e−3 | 1.47 | 5.3e−4 | 1.32 | 2.8e−4 | 1.19 | 3.8e−4 | 1.09 | 1.3e−3 | 0.99 |
| KIDNEY | 1.0e−2 | 3.04 | 2.6e−3 | 2.66 | 8.6e−4 | 2.36 | 8.0e−4 | 2.11 | 2.2e−3 | 1.90 |
| LIVER | 5.4e−2 | 0.83 | 1.2e−2 | 0.76 | 3.4e−3 | 0.70 | 2.0e−3 | 0.65 | 3.0e−3 | 0.60 |
| LUNG | 2.7e−2 | 2.41 | 7.1e−3 | 2.30 | 2.0e−3 | 2.21 | 1.4e−3 | 2.12 | 2.8e−3 | 2.04 |
| PANCREAS | 1.0e−2 | 3.04 | 2.6e−3 | 2.66 | 8.6e−4 | 2.36 | 8.0e−4 | 2.11 | 2.2e−3 | 1.90 |
| SPLEEN | 5.4e−2 | 0.83 | 1.3e−2 | 0.76 | 3.4e−3 | 0.70 | 2.0e−3 | 0.65 | 3.0e−3 | 0.60 |
| STOMACH | 1.8e−3 | 1.74 | 6.0e−4 | 1.60 | 3.8e−4 | 1.48 | 5.7e−4 | 1.38 | 2.0e−3 | 1.29 |

*Unit: mm$^{-1}$

Figure 3:
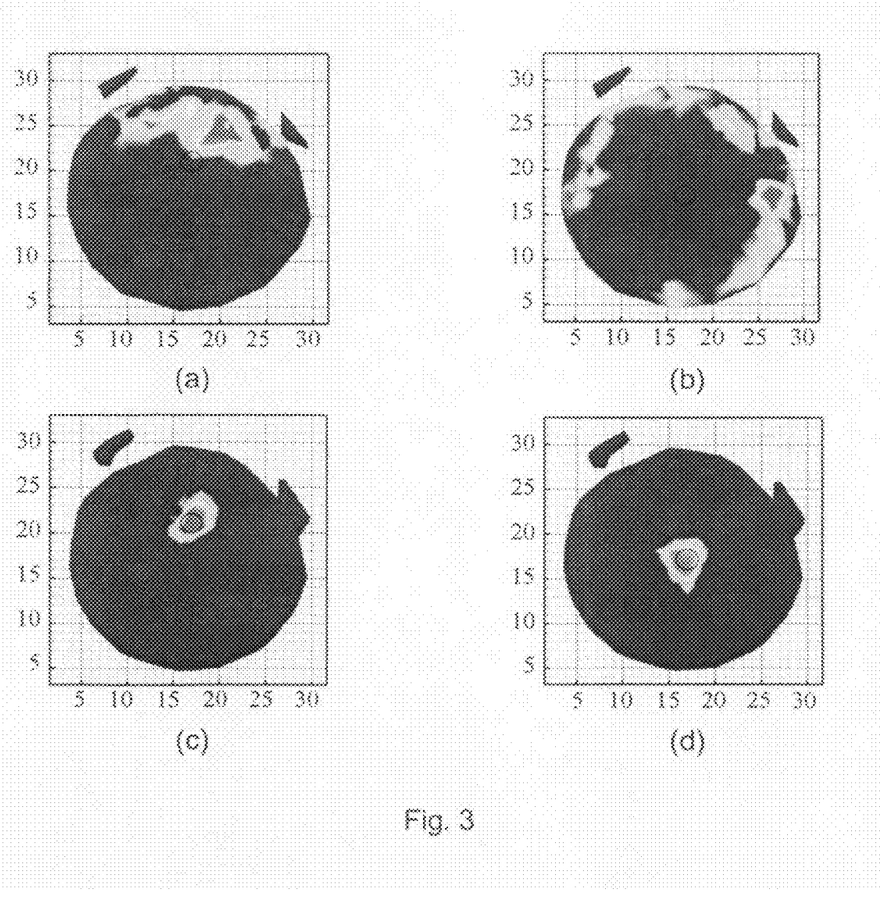
FIG. 3 shows the BLT reconstructed results with single-spectral data and multi-spectral data, in which (a) and (b) are results with single-spectral data, the sources are respectively located at the middle point of the radius and the center; (c) and (d) are spectrally resolved BLT reconstructed results.
Figure 4:
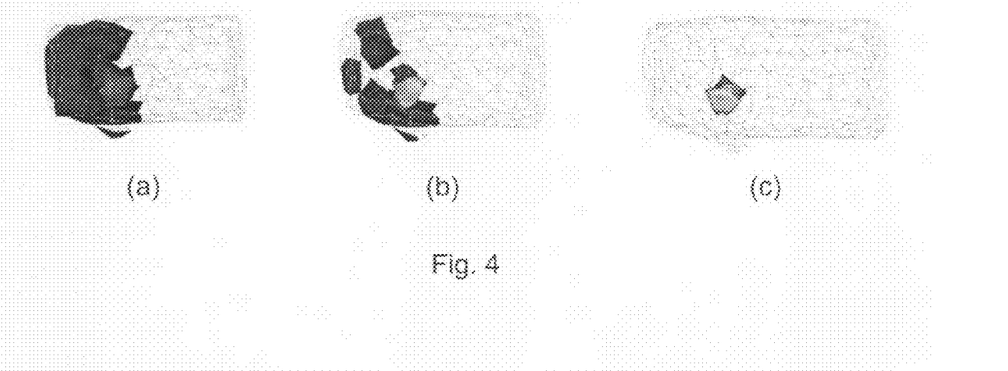
FIG. 4 dramatically shows the evolution of surface mesh and reconstructed results when the source is placed at the middle point of the radius.

The corresponding reconstructed results are shown in FIG. 3. Using the proposed algorithm and monochromatic measurement, BLT reconstructions are performed when the sources are placed at half-radius and center positions. FIGS. 3(a) and (b) demonstrate the reconstructed results. The reconstructed results are not correct because of the absence of a priori information. When the source depth is increasing, the reconstruction is worse. When a priori information of multi-spectral is use, the reconstructed results are improved. BLT reconstructions are performed when the sources were placed at half-radius and center position. FIGS. 3(c) and 3(d) demonstrate the reconstructed results via two mesh evolutions. FIGS. 4(a), (b) and (c) show the evolution of mesh and reconstructed results when the source is placed at half-radius position.

Figure 5:
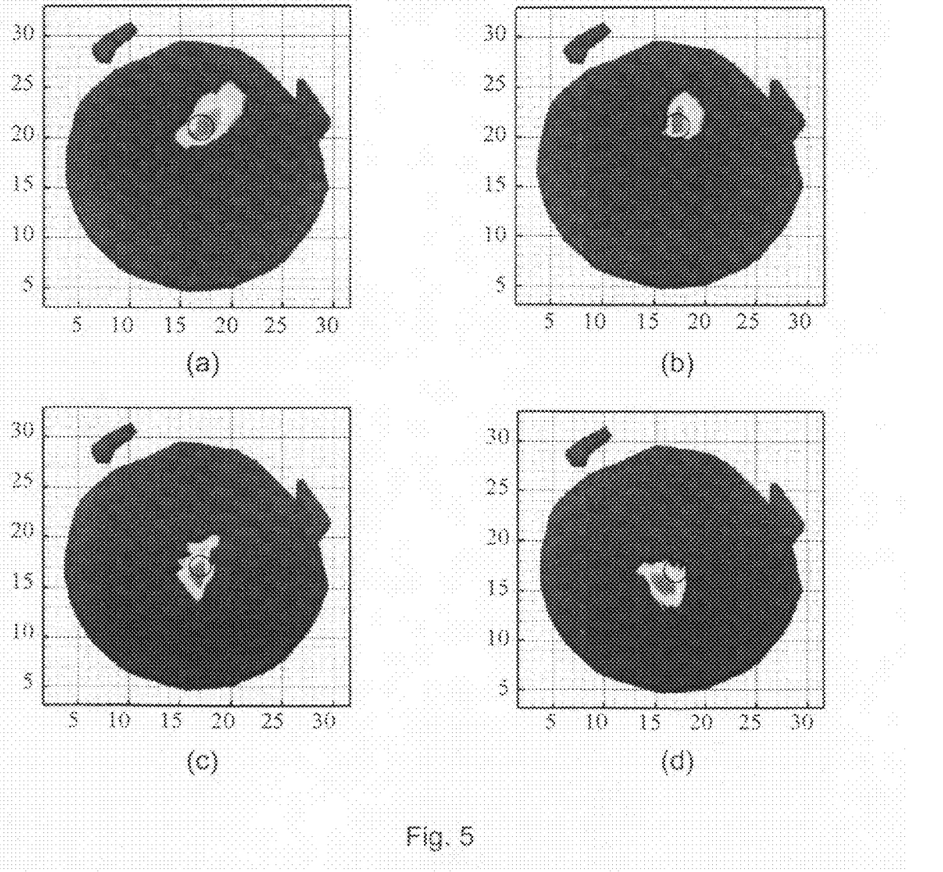
FIG. 5 shows the BLT reconstructed results with the proposed algorithm in view of optical property errors, in which (a) and (b) are the reconstructed results corresponding to +50% and −50% optical property errors for all tissues when the bioluminescent source is located at the middle point of the radius in the mouse phantom; (c) and (d) are the counterparts when the source is located at the mouse's center.

For verifying the method further, the variation of optical properties is considered in the following experiment. In vivo small animal experiments require simultaneous measurement of optical properties, so some errors may be led into our measurement. In this experiment, ±50% errors for all tissues are considered for BLT reconstruction. When the source located at half-radius position, the desirable reconstructed results for the underestimation and overestimation of optical properties are similar with that for the accurate optical properties based on the method proposed herein. Corresponding to +50% and −50% optical property errors for all tissues, when the bioluminescent source is located at half-radius position in the mouse phantom, the reconstructed results are shown in FIGS. 5(a) and 5(b). While the depth of the source is increasing, source reconstruction is more and more affected by optical property errors, FIGS. 5(c) and 5(d) show the reconstructed results when the source located at the center of mouse. From the above figures, however, a small error occurs in the position reconstruction, the reconstructed result is better than former methods without considering the multi-spectral property. This experiment reveals the robustness of the proposed method.

Although illustrative embodiments have been described herein in detail, those skilled in the art will appreciate that variations may be made without departing from the spirit and scope of this invention. Moreover, unless otherwise specifically stated, the terms and expressions used herein are terms of description and not terms of limitation, and are not intended to exclude any equivalents of the systems and methods set forth in the following claims.

What is claimed is:

1. An adaptive-finite-element-based multi-spectral reconstruction method, comprising: performing the adaptive-finite-element-based multi-spectral reconstruction by a processor by utilizing a posteriori permissible source region selection strategy according to a priori knowledge about multi-spectral information of a bioluminescent source and an anatomical structure and optical parameters of a given domain to be reconstructed, wherein the method comprises the following steps:
    Step 1: on the $(l-1)^{th}$ ($l>1$) mesh level of the given domain to be reconstructed, a single-spectral diffusion equation is discretized into a linear equation based on the finite element method;
    Step 2: based on the selection of a posteriori permissible source region, linear relations between unknown source variables and boundary measured data are established on respective single-spectral bands, and the relations on the respective single-spectral bands are combined into a uniform equation reflecting the multi-spectral bands by using the spectral characteristic of the bioluminescent source;

Step 3: an optimization objective function is defined according to the regularization method, and then the spectral projected gradient-based large-scale optimization algorithm is used to optimize the objective function so as to obtain reconstructed results of the $(l-1)^{th}$ level;

Step 4: a single-spectral surface light density distribution is calculated by employing the aforementioned reconstructed results, and it is determined whether the reconstruction process shall be terminated or not according to stopping criteria, wherein if any one of the stopping criteria is satisfied, the reconstruction process is terminated;

Step 5: otherwise, if none of the criteria is satisfied, the permissible source region is reselected according to a posteriori error estimations, and the permissible and forbidden source regions are refined adaptively;

Step 6: the $(l-1)^{th}$ level is transformed into the $l^{th}$ level, the parameters are adjusted, and then the method returns to the Step 1 to continue the reconstruction process.

2. The method according to claim 1, wherein the uniform equation reflecting the multi-spectral bands is obtained by using the spectral characteristic of the bioluminescent source and a posteriori permissible source region selection strategy:

$$\Phi_l^{meas} = F_l W_l^S S_l$$

where $\Phi_l^{meas}$ and $S_l$ are respectively the boundary measured data and the unknown source variables of the $l^{th}$ level in the multi-spectral bands; $F_l$ expresses the relations between the boundary measured data and the unknown source variables in the multi-spectral bands; and $W_l^S$ is used to select a posteriori permissible source region, and further these variables have the following concrete forms:

$$\Phi_l^{meas} = \begin{bmatrix} \Phi_l^{meas}(wb_1) \\ \Phi_l^{meas}(wb_2) \\ \vdots \\ \Phi_l^{meas}(wb_K) \end{bmatrix}, \quad F_l = \begin{bmatrix} \omega(wb_1)f_l(wb_1) \\ \omega(wb_2)f_l(wb_2) \\ \vdots \\ \omega(wb_K)f_l(wb_K) \end{bmatrix}$$

$$W_l^S = \mathrm{Diag}\left(w_{l(11)}^S, w_{l(22)}^S, \ldots, w_{l(ii)}^S, \ldots, w_{l(N_{P_l} N_{P_l})}^S\right),$$

$$w_{l(ii)}^S = \begin{cases} 0 & \{s'_{l(i)} < \gamma_{sp}^{(l)} s_l'^{max}, l > 1\} \\ 1 & \{l = 1\} \text{ or } \{s'_{l(i)} \geq \gamma_{sp}^{(l)} s_l'^{max}, l > 1\} \end{cases}$$

where, $\omega(wb_k)$ is the energy percentage of the $k^{th}$ discretized spectral band of the bioluminescent source, satisfying $$\omega(wb_k) \geq 0 \text{ and } \sum_{k=1}^{K} \omega(wb_k) \approx 1; \Phi_l^{meas}(wb_k)$$

and $f_l(wb_k)$ are the boundary measured data and the unknown source variables in the $k^{th}$ spectral band of the $l^{th}$ level respectively; and $s'_{l(i)}$ and $s_l'^{max}$ are initial reconstructed results of the $l^{th}$ level which are obtained by interpolating the reconstructed results of the $(l-1)^{th}$ level and a maximum value respectively, that is:

$$S'_l = I_{l-1}^l S_{l-1} r (l>1)$$

where $\gamma_{sp}^{(l)}$ is the ratio factor to determine the size of the permissible source region of the $l^{th}$ level.

3. The method according to claim 1, wherein it is determined whether the reconstruction process shall be terminated by considering the following three measure criteria: an error between the boundary measured data and the calculated value, a gradient $g_{\Phi_l}^{(l)}$ in the optimization of each level, and an upper limit of the reconstruction level l, in concrete:

$$\|\Phi_l^{meas}(wb_k) - \Phi_l^c(wb_k)\| < \epsilon_\Phi, \|g_{101_l}^{(l)}\| < \epsilon_g \text{ or } l \geq L_{max},$$

where $\Phi_l^{meas}(wb_k)$ and $\Phi_l^c(wb_k)$ are the boundary measured data in the $k^{th}$ spectral band of the $l^{th}$ discretized level and the corresponding calculated value respectively; and $\epsilon_\Phi$, $\epsilon_g$ and $L_{max}$ are corresponding measurement thresholds respectively.

4. The method according to claim 1, wherein in the permissible and forbidden source regions, a mesh to be refined is selected according to the hierarchical defect correction based a posteriori error estimation method and the direct maximum selection method respectively.

5. The method according to claim 1, wherein in the forbidden source region, the selection of the mesh is performed by only using the error estimations in the single-spectral band, thereby accelerating the reconstruction process.

* * * * *